(12) United States Patent
Vaporciyan et al.

(10) Patent No.: US 10,640,609 B2
(45) Date of Patent: May 5, 2020

(54) METHOD FOR PREPARING A MELT POLYCARBONATE

(71) Applicant: SHELL OIL COMPANY, Houston, TX (US)

(72) Inventors: Garo Garbis Vaporciyan, Houston, TX (US); Kunquan Yu, Katy, TX (US)

(73) Assignee: SHELL OIL COMPANY, Houston, TX (US)

( * ) Notice: Subject to any disclaimer, the term of this patent is extended or adjusted under 35 U.S.C. 154(b) by 53 days.

(21) Appl. No.: 16/064,400

(22) PCT Filed: Dec. 20, 2016

(86) PCT No.: PCT/US2016/067672
§ 371 (c)(1),
(2) Date: Jun. 20, 2018

(87) PCT Pub. No.: WO2017/112627
PCT Pub. Date: Jun. 29, 2017

(65) Prior Publication Data
US 2018/0371162 A1 Dec. 27, 2018

Related U.S. Application Data

(60) Provisional application No. 62/270,725, filed on Dec. 22, 2015.

(51) Int. Cl.
| | | |
|---|---|---|
| *C08G 64/00* | (2006.01) | |
| *C08G 64/30* | (2006.01) | |
| *C07C 68/06* | (2020.01) | |
| *C08L 69/00* | (2006.01) | |

(52) U.S. Cl.
CPC ............ *C08G 64/305* (2013.01); *C07C 68/06* (2013.01); *C08G 64/307* (2013.01); *C08L 69/00* (2013.01); *C08G 2105/00* (2013.01)

(58) Field of Classification Search
USPC .................................................. 528/196, 198
See application file for complete search history.

(56) References Cited

U.S. PATENT DOCUMENTS

| | | | |
|---|---|---|---|
| 4,096,168 | A | 6/1978 | Hallgren |
| 4,892,822 | A | 1/1990 | Abramowicz et al. |
| 5,354,923 | A | 10/1994 | Schon et al. |
| 5,589,564 | A | 12/1996 | Komiya et al. |
| 7,041,775 | B2 | 5/2006 | Martinez et al. |
| 7,763,745 | B2 | 7/2010 | Van Der Heide et al. |
| 2004/0152861 | A1 | 8/2004 | Nefzger et al. |

FOREIGN PATENT DOCUMENTS

| | | |
|---|---|---|
| CN | 1035618 C | 8/1997 |
| CN | 1852938 A | 10/2006 |
| CN | 101484498 A | 7/2009 |
| CN | 100560634 C | 11/2009 |
| EP | 0807656 A1 | 11/1997 |
| EP | 1134248 A1 | 9/2001 |
| JP | 6416826 A | 1/1989 |
| JP | 2001192497 A | 7/2001 |
| WO | 2014189879 A1 | 11/2014 |

OTHER PUBLICATIONS

International Search Report and Written Opinion received for PCT Patent Application No. PCT/US2016/067672, dated Mar. 28, 2017, 8 pages.
International Search Report and Written Opinion received for PCT Patent Application No. PCT/US2016/067664, dated Mar. 29, 2017, 10 pages.
International Search Report and Written Opinion received for PCT Patent Application No. PCT/US2016/067666, dated Mar. 28, 2017, 8 pages.
International Search Report and Written Opinion received for PCT Patent Application No. PCT/US2016/067659, dated Mar. 21, 2017, 10 pages.

*Primary Examiner* — Terressa Boykin
(74) *Attorney, Agent, or Firm* — James D. Carruth

(57) ABSTRACT

A process for producing polycarbonate comprising: a) contacting a dialkyl carbonate with a dihydroxy compound in an oligomerization zone in the presence of an oligomerization catalyst under oligomerization conditions to form a first intermediate; and b) contacting the first intermediate with a diaryl carbonate in a polymerization zone in the presence of a polymerization catalyst under polymerization conditions to produce the polycarbonate wherein the molar ratio of dihydroxy compound to dialkyl carbonate in the oligomerization zone is at least 2:1.

16 Claims, No Drawings

METHOD FOR PREPARING A MELT POLYCARBONATE

CROSS REFERENCE TO RELATED APPLICATIONS

This is a national stage application of International application No. PCT/US2016/067672, filed Dec. 20, 2016, which claims benefit of priority of U.S. application No. 62/270,725, filed Dec. 22, 2015.

FIELD OF THE INVENTION

This invention relates to a method of producing an oligomer from a dialkyl carbonate and a dihydroxy compound.

BACKGROUND OF THE INVENTION

Aromatic polycarbonate, further referred to herein as polycarbonate, is a widely used raw material in many different manufacturing sectors. Due to the hardness and transparency of the material, it can be applied in applications as diverse as automotive windows and optical lenses. It is believed that the demand for polycarbonate will increase significantly in the coming years, requiring improvements in the production of polycarbonate, particularly in terms of efficiency and environmental impact.

Several processes for the production of polycarbonate are known. For instance, a process including reacting phosgene and 2,2-bis(4-hydroxyphenyl)propane (BPA) under phase transfer conditions is applied on an industrial scale. However, this process has the inherent drawbacks of employing the toxic component phosgene and creating chloride containing waste streams.

A different process that does not require the use of phosgene is based on the transesterification of BPA with dialkyl carbonate or diaryl carbonate. The use of a dialkyl carbonate has the disadvantage that in the transesterification with bisphenolacetone, it is not reactive enough under commercially reasonable conditions, to form sufficient quantities of polymeric polycarbonate. Furthermore, the alkyl alcohol that is liberated is not used in any other part of the process for producing polycarbonate, and recycling of the alkyl alcohol to the dialkyl carbonate production requires substantial purification.

The use of a diaryl carbonate, in particular diphenyl carbonate (DPC), has the advantage that it is reactive enough to form polymeric polycarbonate. Furthermore, phenol is liberated in the reaction of the diphenyl carbonate with bisphenolacetone to form polycarbonate, for instance as described in U.S. Pat. No. 5,589,564. This phenol may in turn be recycled to the production of bisphenolacetone or diphenyl carbonate, for which it is a main raw material. Diphenyl carbonate is expensive and it is desirable to find a way to carry out this process without the substantial cost of using large amounts of diphenyl carbonate. The above process for production of polycarbonate leaves ample room for improvement, in particular in view of the raw materials that are used.

JP S64-16826 describes a process for producing polycarbonate comprising three steps. In the first step, bisphenol acetone is reacted with a dialkyl carbonate at a ratio in the range of 1:1 to 1:100. This reaction produces a dialkyl biscarbonate of bisphenol acetone which is then reacted with an equimolar or greater amount of diphenyl carbonate to produce polycarbonate. In the third step, alkyl phenyl carbonate produced as a byproduct is converted to diphenyl carbonate and dialkyl carbonate.

SUMMARY OF THE INVENTION

This invention provides a process for producing polycarbonate comprising: a) contacting a dialkyl carbonate with a dihydroxy compound in an oligomerization zone in the presence of an oligomerization catalyst under oligomerization conditions to form a first intermediate; and b) contacting the first intermediate with a diaryl carbonate in a polymerization zone in the presence of a polymerization catalyst under polymerization conditions to produce the polycarbonate wherein the molar ratio of dihydroxy compound to dialkyl carbonate in the oligomerization zone is at least 2:1.

DETAILED DESCRIPTION OF THE INVENTION

The invention provides a new way to form polycarbonate. The process comprises contacting a dihydroxy capped carbonate with a diaryl carbonate. The dihydroxy capped carbonate may be, for example a carbonate with a BPA molecule on each end, and the diaryl carbonate may be diphenyl carbonate. This allows for the production of polycarbonate by using less diaryl carbonate than similar known processes because the use of a dihydroxy capped carbonate requires less of the diaryl carbonate to be provided. The dihydroxy capped carbonate is produced by a process comprising contacting an excess of a dihydroxy compound with a dialkyl carbonate to produce the oligomer. In this application, the oligomer may be a monomer or more than one monomer linked together.

The dihydroxy capped carbonate is a carbonate with a dihydroxy compound on each end. The dihydroxy compound may be an aliphatic diol, an acid or a dihydroxy aromatic compound. The dihydroxy capped carbonate may have the formula I.

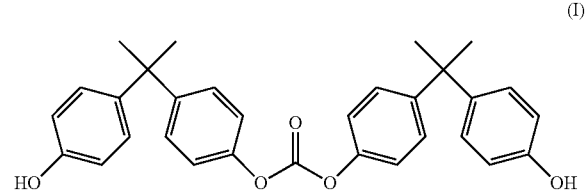 [SMILES: CC(C)(c1ccc(O)cc1)c1ccc(OC(=O)Oc2ccc(C(C)(C)c3ccc(O)cc3)cc2)cc1]

(I)

The dihydroxy capped carbonate may be formed by the reaction of a dihydroxy compound with a dialkyl carbonate. The dihydroxy compound on each end will correspond to the dihydroxy compound used in this reaction and the carbonate moiety will correspond to the dialkyl carbonate used in this reaction.

The dihydroxy compound used to form the dihydroxy capped carbonate may comprise one or more aliphatic diols. Embodiments of suitable aliphatic diols include: isosorbide; 1,4:3,6-dianhydro-D-sorbitol; tricyclodecane-dimethanol; 4,8-bis(hydroxymethyl) tricyclodecane; tetramethylcyclobutanediol; 2,2,4,4-tetramethylcyclobutane-1,3-diol; cis/trans-1,4-cyclohexanedimethanol; cyclohex-1,4-ylenedimethanol; trans-1,4-cyclohexanedimethanol; trans-1,4-bis (hydroxymethyl) cyclohexane; cis-1,4-cyclohexanedimethanol; cis-1,4-bis(hydroxymethyl) cyclohexane; cis-1,2-cyclohexanedimethanol; 1,1'-bi(cyclohexyl)-4,4'-diol; dicyclohexyl-4,4'-diol; 4,4'-di-hydroxybicyclohexyl; and poly(ethylene glycol).

The dihydroxy compound used to form the dihydroxy capped carbonate may comprise one or more acids. Embodiments of suitable acids include: 1,10-dodecanoic acid; adipic acid; hexanedioic acid, isophthalic acid; 1,3-benzenedicarboxylic acid; teraphthalic acid; 1,4-benzenedicarboxylic acid; 2,6-naphthalenedicarboxylic acid; 3-hydroxybenzoic acid; and 4-hydroxybenzoic acid.

The dihydroxy compound used to form the dihydroxy capped carbonate may comprise one or more dihydroxy aromatic compounds. A dihydroxy aromatic compound is an aromatic compound comprising two hydroxyl groups on one or more aromatic rings. Examples of dihydroxy aromatic compounds include bisphenol, for example, BPA, which is a preferred dihydroxy aromatic compound and dihydroxy benzene, for example resorcinol.

Dihydroxy aromatic compounds can be bisphenols having one or more halogen, nitro, cyano, alkyl, or cycloalkyl groups. Embodiments of suitable bisphenols include 2,2-bis (4-hydroxyphenyl) propane (BPA); 2,2-bis(3-chloro-4-hydroxyphenyl) propane; 2,2-bis(3-bromo-4-hydroxyphenyl) propane; 2,2-bis(4-hydroxy-3-methylphenyl) propane; 2,2-bis (4-hydroxy-3-isopropylphenyl) propane; 2,2-bis(3-t-butyl-4-hydroxyphenyl) propane; 2,2-bis(3-phenyl-4-hydroxyphenyl) propane; 2,2-bis(3,5-dichloro-4-hydroxyphenyl) propane; 2,2-bis(3,5-dibromo-4-hydroxyphenyl) propane; 2,2-bis(3,5-dimethyl-4hydroxyphenyl) propane; 2,2-bis(3-chloro-4-hydroxy-5-methylphenyl) propane; 2,2-bis(3-bromo-4-hydroxy-5-methylphenyl) propane; 2,2-bis(3-chloro-4-hydroxy-5-isopropylphenyl) propane; 2,2-bis(3-bromo-4-hydroxy-5-isopropylphenyl) propane; 2,2-bis(3-t-butyl-5-chloro-4-hydroxyphenyl) propane; 2,2-bis(3-bromo-5-t-butyl-4-hydroxyphenyl) propane; 2,2-bis(3-chloro-5-phenyl-4-hydroxyphenyl) propane; 2,2-bis(3-bromo-5-phenyl-4-hydroxyphenyl) propane; 2,2-bis(3,5-di-isopropyl-1-4-hydroxyphenyl) propane; 2,2-bis(3,5-di-t-butyl-4-hydroxyphenyl) propane; 2,2-bis(3,5-diphenyl-4-hydroxyphenyl) propane; 2,2-bis(4-hydroxy-2,3,5,6-tetrachlorophenyl) propane; 2,2-bis(4-hydroxy-2,3,5,6-tetrabromophenyl) propane; 2,2-bis(4-hydroxy-2,3,5,6-tetramethylphenyl) propane; 2,2-bis(2,6-dichloro-3,5-dimethyl-4-hydroxyphenyl) propane; 2,2-bis(2,6-dibromo-3,5-dimethyl-4-hydroxyphenyl) propane; 1,1-bis(4-hydroxyphenyl) cyclohexane; 1,1-bis(3-chloro-4-hydroxyphenyl) cyclohexane; 1,1-bis(3-bromo-4-hydroxyphenyl) cyclohexane; 1,1-bis(4-hydroxy-3-methylphenyl) cyclohexane; 1,1-bis(4-hydroxy-3-isopropylphenyl) cyclohexane; 1,1-bis(3-t-butyl-4-hydroxyphenyl) cyclohexane; 1,1-bis (3-phenyl-4-hydroxyphenyl) cyclohexane; 1,1-bis(3,5-dichloro-4-hydroxyphenyl) cyclohexane; 1,1-bis (3,5-dibromo-4-hydroxyphenyl) cyclohexane; 1,1-bis(3,5-dimethyl-4-hydroxyphenyl) cyclohexane; 1,1-bis (3-chloro-4-hydroxy-5-methylphenyl) cyclohexane; 1,1-bis(3-bromo-4-hydroxy-5-methylphenyl) cyclohexane; 1,1-bis(3-chloro-4-hydroxy-5-isopropylphenyl) cyclohexane; 1,1-bis(3-bromo-4-hydroxy-5-isopropylphenyl) cyclohexane; 1,1-bis(3-t-butyl-5-chloro-4-hydroxyphenyl) cyclohexane; 1,1-bis (3-bromo-5-t-butyl-4-hydroxyphenyl) cyclohexane; 1,1-bis (3-chloro-5-phenyl-4-hydroxyphenyl) cyclohexane; 1,1-bis(3-bromo-5-phenyl-4-hydroxyphenyl) cyclohexane; 1,1-bis(3,5-di isopropyl-4-hydroxyphenyl) cyclohexane; 1,1-bis(3,5-di-t-butyl-4-hydroxyphenyl) cyclohexane; 1,1-bis(3,5-diphenyl-4-hydroxyphenyl) cyclohexane; 1,1-bis(4-hydroxy-2,3,5,6-tetrachlorophenyl) cyclohexane; 1,1-bis(4-hydroxy-2,3,5,6-tetrabromophenyl) cyclohexane; 1,1-bis(4-hydroxy-2,3,5,6-tetramethylphenyl) cyclohexane; 1,1-bis(2,6-dichloro-3,5-dimethyl-4-hydroxyphenyl) cyclohexane; 1,1-bis(2,6-dibromo-3,5-dimethyl-4-hydroxyphenyl) cyclohexane; 1,1-bis(4-hydroxyphenyl)-3,3,5-trimethylcyclohexane; 1,1-bis (3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis (3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis (3,5-dimethyl-4-hydroxyphenyl)-3,3,5-trimethylcyclohexane; 1,1-bis (3-chloro-4-hydroxy-5-methylphenyl)-3,3,5-trimethylcyclohexane; 1,1-bis(3-bromo-4-hydroxy-5-methylphenyl)-3,3,5-trimethylcyclohexane; 1,1-bis (3-chloro-4-hy-droxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-di-isopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4'-dihydroxy-1,1-biphenyl; 4,4'-dihydroxy-3,3'-dimethyl-1,1-biphenyl; 4,4'-dihydroxy-3,3'-dioctyl-1,1-biphenyl; 4,4'-dihydroxydiphenylether; 4,4'-dihydroxydiphenylthioether; 1,3-bis (2-(4-hydroxyphenyl)-2-propyl) benzene; 1,3-bis(2-(4-hydroxy-3-methylphenyl)-2-propyl) benzene; 1,4-bis(2-(4-hydroxyphenyl)-2-propyl) benzene and 1,4-bis(2-(4-hydroxy-3-methylphenyl)-2-propyl) benzene.

Embodiments of suitable dihydroxy benzenes include hydro-quinone, resorcinol, methylhydroquinone, butylhydro-quinone, phenylhydroquinone, 4-phenylresorcinol and 4-methylresorcinol.

Embodiments of suitable dihydroxy naphthalenes include 2,6-dihydroxy naphthalene; 2,6-dihydroxy-3-methyl naphthalene; 2,6-dihydroxy-3-phenyl naphthalene; 1,4-dihydroxy naphthalene; 1,4-dihydroxy-2-methyl naphthalene; 1,4-dihydroxy-2-phenyl naphthalene and 1,3-dihydroxy naphthalene.

In one embodiment, the dialkyl carbonate is represented by the formula $R^1OCOOR^1$. In another embodiment, the dialkyl carbonate is represented by the formula $R^1OCOOR^2$. $R^1$ and $R^2$ represent an alkyl group having 1 to 10 carbon atoms, an alicyclic group having 3 to 10 carbon atoms or an aralkyl group having 6 to 10 carbon atoms. Examples of $R^1$ and $R^2$ include an alkyl group, such as methyl, ethyl, propyl, allyl, butyl, butenyl, pentyl, hexyl, heptyl, octyl, nonyl, decyl and cyclohexylmethyl and isomers thereof. Further examples of $R^1$ and $R^2$ include an alicyclic group, such as cyclopropyl, cyclobutyl, cyclopentyl, cyclohexyl, and cycloheptyl; and an aralkyl group, such as benzyl, phenethyl, phenylpropyl, phenylbutyl, methylbenzyl and isomers thereof.

The alkyl, alicyclic or aralkyl group may be substituted with a substituent such as a lower alkyl group, a lower alkoxy group, a cyano group and a halogen atom.

Examples of the dialkyl carbonate where the alkyl groups are the same are dimethyl carbonate, diethyl carbonate, dipropyl carbonate, diallyl carbonate, dibutenyl carbonate, dibutyl carbonate, dipentyl carbonate, dihexyl carbonate, diheptyl carbonate, dioctyl carbonate, dinonyl carbonate, didecyl carbonate, dicyclopentyl carbonate, dicyclohexyl carbonate, dicycloheptyl carbonate, and isomers thereof.

Examples of the dialkyl carbonate where the alkyl groups are different are methylethyl carbonate, methylpropyl carbonate, methylbutyl carbonate, methylbutenyl carbonate, methylpentyl carbonate, methylhexyl carbonate, methylheptyl carbonate, methyloctyl carbonate, methylnonyl carbonate, and methyldecyl carbonate and isomers thereof. Further examples include any combination of alkyl groups having 1 to 10 carbon atoms, for example, ethylpropyl carbonate, ethylbutyl carbonate, propylbutyl carbonate and isomers thereof.

A dialkyl carbonate where $R^1$ and/or $R^2$ is an alkyl group having four or less carbon atoms is preferred. The dialkyl carbonate is most preferably diethyl carbonate.

The dialkyl carbonate may be produced by any method known to one of ordinary skill in the art. For example, the dialkyl carbonate may be produced by the method described in U.S. Pat. No. 7,763,745 where an alkylene carbonate and an alkanol feedstock are introduced into a reaction zone to react in the presence of a transesterification catalyst to yield an alkanediol-rich stream and a stream comprising dialkyl carbonate and alkanol which streams are separated by one or more steps to produce a dialkyl carbonate rich stream.

The oligomerization catalyst used in the reaction of these reactants can be any known transesterification catalyst. The catalyst can be heterogeneous or homogeneous. In another embodiment, both heterogeneous and homogeneous catalysts may be used.

The polymerization catalyst used in the reaction of these reactants can be heterogeneous or homogeneous. In another embodiment, both heterogeneous and homogeneous catalysts may be used.

The same catalyst can be used for the oligomerization and polymerization steps. In another embodiment, different catalysts may be used for the oligomerization and polymerization steps. In one embodiment, a heterogeneous catalyst is used in the oligomerization step, and a different catalyst, either homogeneous or heterogeneous is used in the polymerization step.

The catalyst may include hydrides, oxides, hydroxides, alcoholates, amides or salts of alkali metals, i.e., lithium, sodium, potassium, rubidium and cesium. The catalyst may be a hydroxide or alcoholate of potassium or sodium. Other suitable catalysts are alkali metal salts, for example, acetates, propionates, butyrates or carbonates, for example sodium acetate. In addition, derivatives of ethylene diamine tetraaectic acid, such as EDTA tetrasodium salt and EDTA magnesium disodium salt and combinations thereof may be used. Other suitable catalysts comprise a source of alkaline earth metal ions, for example, magnesium hydroxide or calcium hydroxide or mixtures thereof.

The catalyst can comprise salt(s) of a non-volatile inorganic acid, for example, salts of a non-volatile inorganic acid such as $NaH_2PO_3$, $NaH_2PO_4$, $KH_2PO_4$, $CsH_2PO_4$, $Cs_2H_2PO_4$ or mixtures thereof. Alternatively, the catalyst can comprise mixed alkali metal salt(s) of phosphoric acid, such as $NaKHPO_4$, $CsNaHPO_4$, $CsKHPO_4$ and mixtures thereof.

Further suitable catalysts include phosphines, arsines or divalent sulfur compounds and selenium compounds and onium salts thereof. Examples of this type of catalyst includes tributylphosphine; triphenylphosphine; diphenylphopsphine; 1,3-bis(diphenylphosphino) propane; triphenylarsine; trimethylarsine; tributylarsine; 1,2-bis(diphenylarsino) ethane; triphenylantimony; diphenylsulfide; diphenyldisulfide; diphenylselenide; tetraphenylphosphonium halide (Cl, Br, I); tetraphenylarsonium halide (Cl, Br, I); triphenylsulphonium halide (Cl, Br, I). The catalyst may comprise quaternary ammonium compounds, quaternary phosphonium compounds or a combination thereof. For example, the catalyst may comprise tetramethyl phosphonium hydroxide, tetramethyl phosphonium acetate, tetramethyl phosphonium formate, tetrabutyl phosphonium hydroxide, tetrabutyl phosphonium acetate, tetraphenyl phosphonium acetate, tetraphenyl phosphonium phenoxide and combinations thereof.

Additional suitable catalysts include complexes or salts of tin, titanium or zirconium. Examples of this type of catalyst include butylstannonic acid; tin methoxide; dimethyltin; dibutyltin oxide; dibutyltin dilaurate; tributyltin hydride; tributyltin chloride; tin(II) ethylhexanoates; zirconium alkoxides (methyl, ethyl or butyl); zirconium (IV) halides (F, Cl, Br, I); zirconium nitrates; zirconium acetylacetonate; titanium alkoxides (methyl, ethyl or isopropyl); titanium acetate; titanium acetylacetonate.

The catalyst may be an ion exchange resin that contains suitable functional groups, for example, tertiary amine groups, quaternary ammonium groups, sulfonic acid groups and carboxylic acid groups. The catalyst may be an alkali metal or alkaline earth metal silicate. The catalyst may comprise an element from Group 4 (such as titanium), Group 5 (such as vanadium), Group 6 (such as chromium or molybdenum) or Group 12 (such as zinc) of the Periodic Table of the Elements, or tin or lead, or a combination of such elements, such as a combination of zinc with chromium (for example zinc chromite). These elements may be present in the catalyst as an oxide, such as zinc oxide.

The catalyst may be selected from the group consisting of sodium hydroxides, sodium carbonates, lithium hydroxides, lithium carbonates, tetraalkylammonium hydroxides, tetraalkylammonium carbonates, titanium alkoxides, lead alkoxides, tin alkoxides and aluminophosphates.

The contacting of the dihydroxy compound and the dialkyl carbonate can take place in a batch, semi-batch or continuous reaction step. The oligomerization reaction may be carried out in any type of reactor, for example, a batch reactor, a batch reactor with a vacuum withdrawal, a batch reactor with a distillation column; or a catalytic distillation column. The reaction is preferably carried out in a reactor that provides for the removal of alcohol during the reaction. The reaction is an equilibrium reaction, and the removal of alcohol shifts the equilibrium in favor of the desired products.

In a catalytic or reactive distillation column, the reaction takes place in the same place that the separation of reactants and products takes place. In this column, there is a reaction zone that can be defined as the portion of the reactive distillation column where catalyst is present. This catalyst may be homogeneous or heterogeneous.

The reaction can be carried out in multiple batch reactors that are operated with their operating cycles out of synchronization. In this way, product would be produced continuously and any further reaction steps could be carried out continuously.

In an embodiment of a semi-batch operation, the dihydroxy compound, the dialkyl carbonate and the catalyst can be combined in a stirred pot reactor. The reactor can be connected to a distillation apparatus that removes alcohol that is formed as part of the reaction. This shifts the equilibrium towards the products and improves the performance of the reaction. If dialkyl carbonate is removed via the distillation apparatus, it can be recycled to the reactor.

The first addition product formed by the reaction is an alkyl-dihydroxy-carbonate intermediate. For example, if the dihydroxy compound is BPA and the dialkyl carbonate is dimethyl carbonate, then the intermediate formed would be methyl-BPA-carbonate.

The intermediate is further reacted, either via disproportionation or via further transesterification with an additional dihydroxy compound. The disproportionation reaction would result in producing dialkyl carbonate. The further transesterification would result in production of a carbonate molecule capped on both ends with a dihydroxy compound.

The overall reaction is conducted with an excess of dihydroxy compound to ensure that there is sufficient dihydroxy compound to produce the dihydroxy capped carbonate. For example, if the dihydroxy compound is BPA and the dialkyl carbonate is dimethyl carbonate, the reaction will produce BPA capped carbonate. This overall reaction is shown below:

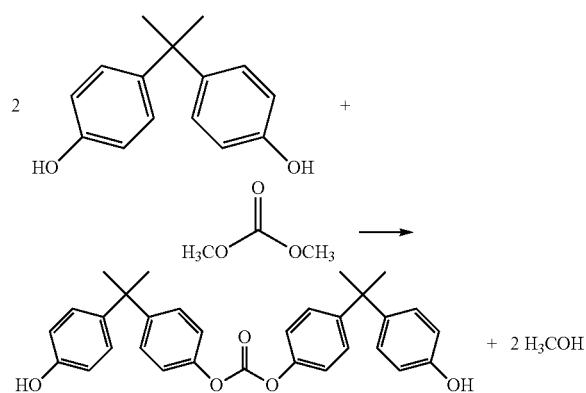

The reaction is carried out to produce as much of the dihydroxy capped carbonate as possible. The first intermediate, alkyl-dihydroxy-carbonate is produced, but the reaction is conducted to minimize the amount of alkyl-dihydroxy-carbonate remaining at the end of the reaction.

The oligomerization conditions of the reaction step can be adjusted to provide for removal of the alcohol formed and also to ensure adequate reaction rates. If the temperature is too high or the pressure too low, then the reactants may be carried out of the reaction zone via the distillation apparatus or side reactions may be promoted.

The oligomerization is preferably carried out at a pressure of less than 2.03 MPa. The pressure is preferably in a range of from 101.3 kPa to 2.03 MPa. The oligomerization is preferably carried out at a temperature in the range of from 110° C. to 330° C., preferably of from 160° C. to 300° C., and most preferably of from 180° C. to 280° C.

Reactor conditions may be changed as the reaction proceeds. Initially, the temperature and pressure need to be such that the temperature is high enough to drive the reaction and evaporate any alcohol formed. The temperature should not be too high as it will also evaporate the dialkylcarbonate before it reacts with the dihydroxy compound. In addition, higher temperatures can result in undesired side reactions.

It is preferred to use an excess of the dihydroxy compound to ensure that the reaction proceeds to produce the dihydroxy capped carbonate. The feed to the reactor comprises a dihydroxy compound and dialkyl carbonate at a molar ratio of at least 2:1. The dihydroxy compound to dialkyl carbonate molar ratio is preferably at least 3:1, more preferably 5:1 and most preferably 10:1. The dihydroxy compound to dialkyl carbonate molar ratio is preferably in a range of from 2:1 to 100:1, preferably in a range of from 5:1 to 50:1.

Due to the excess of dihydroxy compound used, it is preferred to remove some or all of the excess dihydroxy compound after the reaction is conducted and the dihydroxy capped carbonate is formed. This provides for a purer dihydroxy capped carbonate product that can be used in further reaction steps if desired. In another embodiment, the excess dihydroxy compound can be left with the dihydroxy capped carbonate.

Alcohol may be formed during the reaction. For example, if dimethyl carbonate is used as the dialkyl carbonate, then methanol will be formed; and if diethyl carbonate is used as the dialkyl carbonate then ethanol will be formed. In addition, other byproducts may be formed, including isomers of the oligomer.

The oligomer formed in this reaction may be further reacted with the same or a different dialkyl carbonate.

The contacting of the dihydroxy capped carbonate and the diaryl carbonate can take place in a batch, semi-batch or continuous reaction step. The polymerization reaction may be carried out in any type of reactor, for example, a batch reactor, a batch reactor with a vacuum withdrawal, a batch reactor with a distillation column; or a catalytic distillation column. The reaction is preferably carried out in a reactor that provides for the removal of alcohol during the reaction. The reaction is an equilibrium reaction, and the removal of alcohol shifts the equilibrium in favor of the desired products.

In a catalytic or reactive distillation column, the reaction takes place in the same place that the separation of reactants and products takes place. In this column, there is a reaction zone that can be defined as the portion of the reactive distillation column where catalyst is present. This catalyst may be homogeneous or heterogeneous.

The reaction can be carried out in multiple batch reactors that are operated with their operating cycles out of synchronization. In this way, product would be produced continuously and any further reaction steps could be carried out continuously.

In an embodiment of a semi-batch operation, the dihydroxy capped carbonate, the diaryl carbonate and the catalyst can be combined in a stirred pot reactor. The reactor can be connected to a distillation apparatus that removes alcohol that is formed as part of the reaction. This shifts the equilibrium towards the products and improves the performance of the reaction. If diaryl carbonate is removed via the distillation apparatus, it can be recycled to the reactor.

According to a preferred embodiment, the overall reaction is shown below, when the dihydroxy capped carbonate is di-bisphenol acetone-carbonate and the diaryl carbonate is diphenyl carbonate:

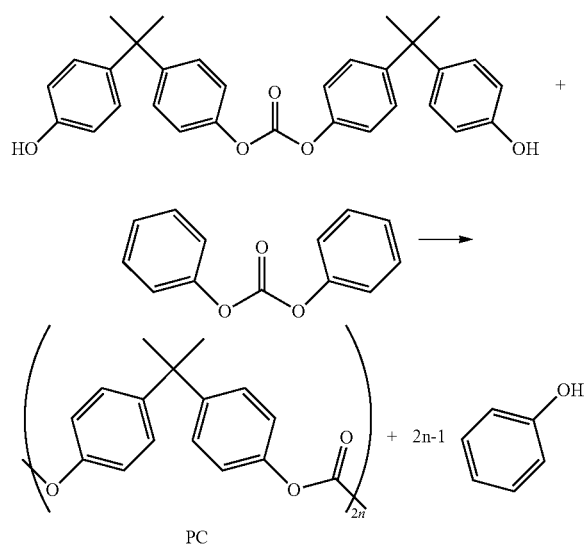

In this embodiment, the polymerization reaction produces higher oligomers and ultimately forms polycarbonate. The reaction also produces phenol which can be recycled to a step for producing the diphenyl carbonate or a dihydroxy aromatic compound.

The polymerization reaction conditions are similar to those used for production of polycarbonate using bisphenolacetone and diphenyl carbonate. The polymerization conditions of the reaction step can be adjusted to provide for removal of the alcohol formed and also to ensure adequate reaction rates. If the temperature is too high or the pressure too low, then the reactants may be carried out of the reaction zone via the distillation apparatus or side reactions may be promoted.

The polymerization is preferably carried out at a pressure of less than 2.03 MPa. The pressure is preferably in a range of from 0.01 kPa to 2.03 MPa, preferably of from 0.1 kPa to 50 kPa. The polymerization is preferably carried out at a temperature in the range of from 170° C. to 350° C., preferably of from 190° C. to 320° C.

The reactor conditions may be changed as the reaction proceeds. Initially, the temperature and pressure need to be such that the temperature is high enough to drive the reaction and evaporate any alcohol formed. In one embodiment, the polymerization reaction is carried out at a temperature in the range of from 190° C. to 320° C. at very low pressures, for example, 0.1 kPa. The temperature is initially at the lower end of this range and as the reaction progresses, the temperature is gradually increased. The pressure is initially at 20 kPa and is gradually decreased to 0.1 kPa. The temperature in the later stages of the reaction needs to be high enough to maintain a sufficiently high melt flow of polymer, which becomes more viscous as the polymerization progresses. The temperature should not be too high as it will also cause undesired side reactions. The pressure needs to be low enough to remove the phenol formed in the reaction from this viscous melt.

Once the polymerization process starts, the reactants may be passed through a plurality of reactors in series. The steps after the initial contact of the dihydroxy capped carbonate and diphenyl carbonate can proceed in a similar method as any known melt polycarbonate process. This includes the design and operation of reactors, and the use of additives that impart useful properties to the resulting polycarbonate.

Since the starting material already comprises a carbonate moiety in the dihydroxy capped carbonate, less diaryl carbonate is required to form the polycarbonate. If a pure stream of dihydroxy capped carbonate is used, then one mole of diaryl carbonate is required for each mole of dihydroxy capped carbonate. The preferred molar ratio of dihydroxy capped carbonate to diaryl carbonate is in the range of from 1:2 to 2:1.

If a slight excess of either the dihydroxy capped carbonate or the diaryl carbonate is added to the reactor, then the resulting polycarbonate will be capped with one or the other of the corresponding compounds. In addition, any additives or other components known to be useful in polycarbonate production can be added to the polymerization reaction.

The regular route to produce melt polycarbonate typically reacts 1 mole of diphenyl carbonate with 1 mole of BPA. The reaction described herein typically comprises reacting 1 mole of diphenyl carbonate with 1 mole of dihydroxy capped carbonate. Therefore, in this reaction, ½ mole of diphenyl carbonate is used to react with 1 mole of BPA.

If the dihydroxy capped carbonate stream contains impurities, for example, dihydroxy aromatic compounds from the manufacture of the dihydroxy capped carbonate, these can also be converted, but will require additional diaryl carbonate.

Alcohol may be formed during the reaction. For example, if diphenyl carbonate is used as the diaryl carbonate, then phenol will be formed. In addition, other byproducts may be formed, including isomers of the starting materials, and the branching of polycarbonate chains from the Fries rearrangement.

EXAMPLES

Example 1

BPA (38.7 g/170 mmol) and DEC (1.65 g/14 mmol) were mixed with 0.056 g of Ti(OEt)$_4$, resulting in a mixture that contained about 290 ppm of Ti. The reaction mixture was heated in an autoclave batch reactor at 180° C. under constant stirring. After one hour, the reaction mixture was cooled to ambient temperature and analyzed using GC and FTIR. The analysis showed that about 15% of the DEC was converted to di-BPA-carbonate. In addition, some of the DEC was converted to ethyl-BPA-carbonate.

Example 2

In yet another example, transesterification between BPA and DMC is performed, and the reaction by product methanol is removed from the reaction system via molecular sieves 4 A. The reaction was performed by refluxing a mixture of BPA (41.2 g/180 mmol) and DMC (1.48 g/16 mmol) in the presence of 0.061 g Ti(OEt)$_4$ (about 300 ppm Ti), methanol was continuously removed over a 5 g molecular sieves 4 A in a Soxhlet extractor. After 1 hr at 180° C., about 26% DMC was converted into di-BPA-carbonate. In addition, some of the DMC was converted to methyl-BPA-carbonate.

Example 3

In this example, a mixture of about 24.5 g of di-bisphenol acetone-carbonate (50.8 mmol) and 6.5 g BPA (28.5 mmol) was mixed with 17.8 g of DPC (83.3 mmol) was polymerized in the presence of 10 ppm of lithium hydroxide. The polymerization was carried out in a batch vacuum distillation setup: a 200 ml glass round bottom flask equipped with a mechanical stirring apparatus including a teflon agitating blade, a precise pressure controller and a heating mantle, as well as a overhead receiver. The reaction mixture was first heated at 200° C. at 300 mbar for 2 hr, and then the temperature was slowly ramped to 260° C. and the pressure was lowered to 0.5 mbar over a 15 min time period. The polymerization conditions were kept at 260° C./0.5 mbar for 1 hr afterwards. Molecular analysis showed the polymer sample has a Mn of 13000.

That which is claimed is:

1. A process for producing polycarbonate comprising:
   a. contacting a dialkyl carbonate with a dihydroxy compound in an oligomerization zone in the presence of an oligomerization catalyst under oligomerization conditions to form a first intermediate; and
   b. contacting the first intermediate with a diaryl carbonate in a polymerization zone in the presence of a polymerization catalyst under polymerization conditions to produce the polycarbonate
      wherein the molar ratio of dihydroxy compound to dialkyl carbonate in the oligomerization zone is at least 2:1, and wherein the dihydroxy compound is a dihydroxy aromatic compound.

2. The process of claim 1, further comprising passing the intermediate from step a) to an additional oligomerization zone to produce an oligomer with a longer chain length than the oligomer from step a).

3. The process claim 1, further comprising passing the polycarbonate from step b) to an additional polymerization zone to produce a polymer with a longer chain length than the polycarbonate from step b).

4. The process of claim 1, wherein the same catalyst is used for step a) and step b).

5. The process of claim 1, further comprising removing at least a portion of any unreacted dihydroxy compound from the first intermediate before reacting the first intermediate in step b).

6. The process of claim 1, wherein an alcohol is formed during the oligomerization.

7. The process of claim 6, further comprising removing at least a portion of the alcohol as an alcohol product stream.

8. The process of claim 1, wherein the dialkyl carbonate is selected from the group consisting of dimethylcarbonate, diethylcarbonate and mixtures thereof.

9. The process of claim 1, wherein the dihydroxy compound is bisphenol acetone.

10. The process of claim 1, wherein the diaryl carbonate is diphenylcarbonate.

11. The process of claim 1, wherein the first intermediate is a di-bisphenol acetone-carbonate compound.

12. The process of claim 1, wherein the molar ratio of dihydroxy compound to dialkyl carbonate in the oligomerization zone is at least 5:1.

13. The process of claim 1, wherein the molar ratio of dihydroxy compound to dialkyl carbonate in the oligomerization zone is at least 10:1.

14. The process of claim 1, wherein the molar ratio of dihydroxy compound to dialkyl carbonate in the oligomerization zone is in the range of from 2:1 to 100:1.

15. The process of claim 1, wherein the molar ratio of the first intermediate to the diaryl carbonate in the polymerization zone is from 1:2 to 2:1.

16. The process of claim 1, further comprising adding additives or other components to the polymerization zone.

* * * * *